US012220706B2

(12) United States Patent
Wang et al.

(10) Patent No.: US 12,220,706 B2
(45) Date of Patent: Feb. 11, 2025

(54) APPARATUS AND METHODS FOR THERMAL CYCLING OF SAMPLE

(71) Applicant: LUMINEX CORPORATION, Austin, TX (US)

(72) Inventors: William S. Wang, Austin, TX (US); Steve Krueger, Austin, TX (US); Douglas Whitman, Austin, TX (US); Blaine Oldham, Austin, TX (US); Tabitha Vanderstoep, Austin, TX (US)

(73) Assignee: LUMINEX CORPORATION, Austin, TX (US)

( * ) Notice: Subject to any disclaimer, the term of this patent is extended or adjusted under 35 U.S.C. 154(b) by 6 days.

(21) Appl. No.: 17/931,973

(22) Filed: Sep. 14, 2022

(65) Prior Publication Data

US 2023/0041131 A1    Feb. 9, 2023

Related U.S. Application Data

(63) Continuation of application No. 16/860,140, filed on Apr. 28, 2020, now abandoned.
(Continued)

(51) Int. Cl.
*B01L 7/00* (2006.01)
*B01L 99/00* (2010.01)
*C12Q 1/686* (2018.01)

(52) U.S. Cl.
CPC ......... *B01L 7/52* (2013.01); *B01L 2300/1805* (2013.01); *B01L 2300/1844* (2013.01); *B01L 2300/1894* (2013.01); *C12Q 1/686* (2013.01)

(58) Field of Classification Search
CPC ............ C12Q 2600/178; C12Q 1/6886; C12Q 2600/136; C12Q 1/686; C12Q 1/6883;
(Continued)

(56) References Cited

U.S. PATENT DOCUMENTS 6,183,693 B1 * 2/2001 Bogen .................... G01N 1/312
422/537
6,403,037 B1 6/2002 Chang et al.
(Continued)

FOREIGN PATENT DOCUMENTS

| WO | WO 2004/029195 | 4/2004 |
| WO | WO 2012/161566 | 11/2012 |
| WO | WO 2013/158740 | 10/2013 |

OTHER PUBLICATIONS

Farrar, et al., "Extreme PCR: efficient and specific DNA amplification in 15-60 seconds," Clin. Chem., 61:145-53, 2015.
(Continued)

*Primary Examiner* — Lydia Edwards
(74) *Attorney, Agent, or Firm* — Parker Highlander PLLC

(57) ABSTRACT

This disclosure relates to apparatus and methods for thermally cycling a sample. Particular embodiments comprise a first pivot arm configured to pivot around a first pivot axis; a second pivot arm configured to pivot around a second pivot axis; a first thermal mass and a second thermal mass coupled to the first pivot arm; and a third thermal mass and a fourth thermal mass coupled to the second pivot arm, wherein the first and third thermal masses are proximal to the sample when the first and second pivot arms are in a first position, and the second and fourth thermal masses are proximal to the sample when the first and second pivot arms are in a second position.

13 Claims, 12 Drawing Sheets

Related U.S. Application Data

(60) Provisional application No. 62/841,390, filed on May 1, 2019.

(58) Field of Classification Search
CPC ........ C12Q 2600/112; C12Q 2600/166; G01N 33/15; G01N 33/57423; B01L 2300/0609; B01L 2300/0816; B01L 2300/087; B01L 2300/1805; B01L 2300/1822; B01L 2300/1827; B01L 2300/1844; B01L 2300/1894; B01L 3/502715; B01L 7/52; B01L 9/527
See application file for complete search history.

(56) References Cited

U.S. PATENT DOCUMENTS

| | | | |
|---|---|---|---|
| 7,466,908 | B1 | 12/2008 | Lem et al. |
| 9,057,568 | B2 | 6/2015 | Malik et al. |
| 2008/0003564 | A1 | 1/2008 | Chen et al. |
| 2008/0057544 | A1 | 3/2008 | Lem et al. |
| 2015/0238968 | A1 | 8/2015 | TerMaat et al. |
| 2016/0289736 | A1 | 10/2016 | Jones et al. |
| 2017/0297028 | A1 | 10/2017 | Jones et al. |
| 2018/0080063 | A1 | 3/2018 | Li et al. |
| 2020/0171503 | A1 | 6/2020 | McFall et al. |
| 2020/0330997 | A1* | 10/2020 | Wei ............................ B01L 9/52 |

OTHER PUBLICATIONS

Fermér, et al., "Microwave-assisted high-speed PCR," *Eur. J. Pharm. Sci.*, 18:129-32, 2003.

Fuchiwaki, et al., "Study of a liquid plug-flow thermal cycling technique using a temperature gradient-based actuator," *Sensors*, 14:20235-44, 2014.

Hühmer, et al., "Noncontact infrared-mediated thermocycling for effective polymerase chain reaction amplification of DNA in nanoliter volumes," *Anal Chem*, 72:5507-12, 2000.

International Search Report and Written Opinion, issued in PCT/US2020/030183, mailed Jul. 27, 2020.

Kopp, et al., "Chemical amplification: continuous-flow PCR on a chip," *Science*, 280:1046-8, 1998.

Li, et al., "Gold nanorod-facilitated localized heating of droplets in microfluidic chips," *Opt. Express*, 21:1281-6, 2013.

Neuzil, et al., "Ultra fast miniaturized real-time PCR: 40 cycles in less than six minutes," *Nucleic Acids Res.*, 34:e77, 2006.

Shaw, et al., "Rapid PCR amplification using a microfluidic device with integrated microwave heating and air impingement cooling," *Lab Chip.*, 10:1725-8, 2010.

Son, et al., "Ultrafast photonic PCR," *Light, Science & Applications*, e280, 2015.

Tanriverdi, et al., "A rapid and automated sample-to-result HIV load test for near-patient application," *J. Infect. Dis.*, S52-8, 2010.

Wittwer, et al., "Extreme PCR: DNA amplification 15-60 seconds," 23rd Annual Symposium on Molecular Pathology, Somerset Inn, Troy, MI (keynote address), Oct. 16, 2014.

Wittwer, et al., "Minimizing the time required for DNA amplification by efficient heat transfer to small samples," *Analytical Biochemistry*, 186:328-331, 1990.

Zhang, et al., "Miniaturized PCR chips for nucleic acid amplification and analysis: latest advances and future trends," *Nucleic Acids Res.*, 35:4223-37, 2007.

* cited by examiner

APPARATUS AND METHODS FOR THERMAL CYCLING OF SAMPLE

CROSS-REFERENCE TO RELATED APPLICATIONS

This application is a continuation of U.S. patent application Ser. No. 16/860,140, filed Apr. 28, 2020, which claims priority to U.S. Provisional Patent Application Ser. No. 62/841,390, filed May 1, 2019, the entire contents of which are incorporated herein by reference.

FIELD OF THE INVENTION

Embodiments of this disclosure relate to apparatus and methods for thermal cycling a sample. Particular embodiments relate to thermally cycling a sample for polymerase chain reaction (PCR) in which, for example, up to 50 cycles of PCR can be completed in less than five minutes.

BACKGROUND

The following descriptions and examples are not admitted to be prior art by virtue of their inclusion within this section.

Certain sample processing techniques, including for example PCR and related processing, utilize thermal cycling by sequentially increasing and decreasing the temperature of the sample for a number of cycles. Particular techniques may employ a significant number of cycles in which the temperature of the sample is maintained within maximum and minimum temperature ranges for specified periods of time during each cycle. Processes utilizing a large number of cycles and extended periods of time within or transitioning between each cycle can take an extended amount of time to complete. Reducing the amount of time needed to transition the sample between the maximum and minimum temperature ranges (and vice versa) can reduce the overall time required to thermally cycle the sample. Reducing the thermal cycling time can reduce the overall sample processing time and provide for more efficient sample processing.

Initially PCR took several hours to perform. Over time, improvements in instrumentation reduced the time needed to perform PCR to under 30 minutes (about 20-60 seconds per cycle). More recently, scientists have been pursuing instrumentation and/or reaction chemistries that will provide PCR amplification in less than 5 minutes. Farrar and Wittwer, for example, reported achieving DNA amplification in under one minute by increasing the primer and polymerase concentrations 10- to 20-fold and rapidly moving the reaction between a hot water bath of 95.5° C. and cool water baths of 25° C.-74° C. (Farrar and Wittwer. "Extreme PCR: efficient and specific DNA amplification in 15-60 seconds." Clinical Chemistry 61.1 (2015): 145-153).

There is a need for devices and methods that can rapidly amplify and detect nucleic acids, particularly in fields such as diagnostics and biothreat detection where the quick and accurate detection of a pathogen is important. While some progress has been made in this regard, improved thermal cycling devices and methods are needed.

SUMMARY

Briefly, the present disclosure provides apparatus and methods for thermal cycling. In certain embodiments, a target nucleic acid is amplified in a disposable molecular diagnostics consumable using ultra-fast polymerase chain reaction (PCR). Ultra-fast thermal cycling for PCR—e.g., 50 cycles in under 5 minutes—may be achieved by repeatedly clamping and releasing a thin sample-containing chip between alternating pairs of thermal masses at different temperatures. Fluorescently-labeled amplicons may be optically detected in the consumable, enabling real-time PCR monitoring during cycling.

One embodiment provides an apparatus for thermal cycling, the apparatus comprising: a retaining member configured to retain a sample module; a first pivot arm configured to pivot around a first pivot axis; a second pivot arm configured to pivot around a second pivot axis; a first thermal mass and a second thermal mass coupled to the first pivot arm; a third thermal mass and a fourth thermal mass coupled to the second pivot arm, wherein: the first thermal mass and the third thermal mass are proximal to the retaining member when the first pivot arm and the second pivot arm are in a first position; and the second thermal mass and the fourth thermal mass are proximal to the retaining member when the first pivot arm and the second pivot arm are in a second position; and a controller configured to control movement of the first pivot arm and the second pivot arm between the first position and the second position.

In certain embodiments, the first thermal mass and the second thermal mass are coupled to the first pivot arm via a first bracket arm. Likewise, in certain embodiments, the third thermal mass and the fourth thermal mass are coupled to the second pivot arm via a second bracket arm. In some embodiments, the apparatus for thermal cycling further comprises at least one actuator. In one embodiment, a first actuator is coupled to the first pivot arm, and a second actuator is coupled to the second pivot arm. In other embodiments, the first pivot arm and the second pivot arm are coupled to a single actuator. In certain embodiments, the apparatus for thermal cycling further comprises a controller that is configured to actuate the actuator or actuators coupled to the first and second pivot arms such that the pivot arms move from the first position to the second position and vice versa.

The thermal masses disclosed herein may be made from thermal conductive materials. In some embodiments, a thermal mass may be made of a metal such as copper, aluminum, or silver. The mass of the first, second, third, and/or fourth thermal mass may be such that it is large enough relative to the sample module (and the sample therein) that within a given thermal cycle, the temperature of the thermal mass would change by less than 2° C., less than 1° C., or less than 0.5° C. By way of illustration, if: (i) the sample module is made of polypropylene and has a mass of 0.59 grams, (ii) the sample has a mass of 0.06 grams and a thermal conductivity substantially the same as water, (iii) the thermal mass is copper, and (iv) the sample module is to be cooled by 35° C. (from 95-60° C.), then a copper mass of at least 47.5 grams would be sufficient to avoid changing the temperature of the copper mass more than 1° C. after contacting and cooling the sample module by 35° C. It should be noted, however, that when the sample module is contacted by two thermal masses, such as by the second and third thermal masses, the 47.5 grams of copper mass could be split between the two thermal masses—e.g., each copper mass could be 23.75 grams.

One pair of thermal masses, e.g., the first thermal mass and the third thermal mass, may function to raise the temperature of the sample in the sample module. These thermal masses may be referred to as heating masses or heating thermal masses. Accordingly, in certain embodiments, the first thermal mass and the third thermal mass each comprise a heating element. In particular embodiments the heating element comprises a thermoelectric cooler (TEC), an electrical resistor, a metal (e.g. nichrome, cupronickel, or other alloys) heating element, a ceramic (e.g. molybdenum disilicide) or a polymer heating element. In certain embodiments, the first thermal mass and the third thermal mass are maintained at a temperature that is at or above a target denaturation temperature during thermal cycling. In certain embodiments, the first thermal mass and the third thermal mass are maintained within a first temperature range from 85° C. to 1300 C, 94° C. to 1300 C, 85° C. to 980 C, 90° C. to 980 C, 94° C. to 105° C., or 94° C. to 98° C. These ranges are merely illustrative, as the desired temperatures may vary depending on the assay during thermal cycling. In certain embodiments, the first thermal mass and the third thermal mass are maintained within the first temperature range, and the temperature at which the first and third thermal masses are maintained within the first temperature range does not change by more than 2° C., 1° C., or 0.5° C., during thermal cycling. The temperature of the first thermal mass and the third thermal mass can be monitored and controlled by one or more temperature sensors and one or more processors.

One pair of thermal masses, e.g., the second thermal mass and the fourth thermal mass, may function to lower the temperature of the sample in the sample module. Accordingly, these thermal masses may be referred to as cooling masses or cooling thermal masses. In some embodiments, the second thermal mass and the fourth thermal mass are maintained within a second temperature range from 15° C. to 700 C, 15° C. to 45° C., 25° C. to 50° C., 50° C. to 70° C., or 58° C. to 62° C. In some embodiments, the second thermal mass and the fourth thermal mass are maintained within the second temperature range, and the temperature at which the second and fourth thermal masses are maintained within the second temperature range does not change by more than 2° C., 1° C., or 0.5° C., during thermal cycling. In particular embodiments, the second thermal mass and the fourth thermal mass are operated at ambient temperature. In certain embodiments, the second thermal mass and the fourth thermal mass are actively cooled by a cooling element such as a thermoelectric cooler or a fan. In particular embodiments, the second and fourth thermal masses are maintained within 2° C., 1° C., or 0.5° C. of the ambient temperature during thermal cycling predominantly by their mass relative to the sample and sample module and passive ventilation of the apparatus or active ventilation of the apparatus by one or more fans circulating ambient temperature air.

In one embodiment, the apparatus is configured such that the first and third thermal masses may be placed in contact with opposing sides of the sample module for a time sufficient to raise the temperature of the sample to a first temperature, the first and third thermal masses are then removed from contact with the sample module, and the second of fourth thermal masses are placed in contact with opposing sides of the sample module for a time sufficient to lower the temperature of the sample to a second temperature. In certain embodiments, the first temperature is a denaturation temperature and the second temperature is an annealing temperature, the sample comprises nucleic acids and reagents for performing PCR, and the sample module is repeatedly and alternatingly contacted with the first and third thermal masses and the second and fourth thermal masses a number of times sufficient to detectably amplify at least one nucleic acid sequence of interest in the sample.

In certain embodiments, the apparatus comprises a retaining member in which the sample module is held during thermal cycling. In one embodiment, the apparatus comprises a frame and the retaining member is mounted on the frame in a position between the first pivot axis and the second pivot axis of the first and second pivot arms, such that the thermal masses can be placed in contact with a sample module in the retaining member, which holds the sample module while not substantially interfering with the ability of the thermal masses to contact at least two sides of the sample module.

One embodiment of the invention provides a sample module. The sample module may comprise an arrangement of channels and chambers disposed in or between two or more layers of material. In one embodiment, the sample module comprises (a) a generally planar core layer having (i) a first major face and a second major face, wherein the first major face and the second major face are on opposite sides of the core layer; (ii) an outer edge face extending around the periphery of the core layer between the first major face and the second major face, wherein at least a portion of the outer edge face is transmissive to light; (iii) at least one cut out that extends through the thickness of the core layer from the first major face to the second major face; (iv) an inner edge face extending at least partially around the cut out, wherein at least a portion of the inner edge face is transmissive to light; and (v) at least one channel formed in the first major face; (b) a first film bonded to the first major face (c) a second film bonded to the second major surface; and (d) an inlet extending through the thickness of the first film; wherein the core layer, the first film, and the second film define a volume at the location of the cut out; wherein the first film covers the channel formed in the first major face; and wherein the channel is in fluid communication with the volume and the inlet.

In certain embodiments, the core layer can be made from a thermopolymer. In some embodiments the core layer is made by injection molding of a thermopolymer. In particular embodiments the core layer has a thickness of about 0.5 to 3 mm, 0.5 to 2 mm, or 0.75 to 1.5 mm. Layers of the sample module that contact the thermal masses of a thermal cycling apparatus, such as the first film and second film described above, can be made of materials that are thin, permit high heat transfer, and are sufficiently flexible to conform to the contacting surface of the thermal mass. In certain embodiments, such layers are made from a thermoplastic polymer or a metal. The thermoplastic polymer may be, for example, a polypropylene, poly(methyl methacrylate) (PMMA), polyethylene, polystyrene, or polyvinylidene fluoride. In particular embodiments, the film has a thickness of about 10 to 50 µm, or 20 to 30 µm.

As mentioned above, the core layer comprises one or more cut outs that extend through the thickness of the core layer. When the first film and the second film are bonded to the first major face and the second major face of the core layer, the first and second films cover the cut out. Together the core layer's inner edge, the first film, and the second film define a volume. The volume is in fluid communication with the channel and the inlet such that a sample can be loaded into the volume via the inlet and channel. The volume can comprise two zones—a sample chamber and an air spring chamber. When a sample is loaded into the sample module, the sample fills the sample chamber zone, and air displaced by the sample is compressed in the air spring chamber zone. In one embodiment, the sample chamber and the air spring chamber form a U shape or asymmetric U shape. Such a U or asymmetric U shape can facilitate the optical interrogation of the sample in the sample chamber through the outer edge of the core layer, particularly in embodiments comprising more than one sample chamber. In the U or asymmetric U shape, the sample can enter and entirely fill at least one arm of the U while compressing air into at least a portion the other arm of the U. When the sample chamber is arranged in this manner, optical excitation and detection of labeled analytes in the reaction chamber can occur through the end of the sample-filled arm of the U. For optical interrogation through the outer edge of the core layer, at least the portion of the core layer is made of a transmissive material, such as a light transmissive thermopolymer, that allows optical excitation and detection of labeled analytes in the reaction chamber.

In some embodiments, at least half of the total empty air volume of the sample module is compressed into one or more air spring chambers once the sample is loaded onto the sample module. In use, a sample can be introduced into the sample module via the inlet and transferred to the sample chamber by applying pressure via the inlet, whereby air displaced from the channel and sample chamber by the sample is compressed in the air spring chamber. In certain embodiments, air is compressed in the air spring chamber at from 5 to 50 pounds-per-square inch gauge (psig), 10 to 30 pounds-per-square inch gauge (psig), or 15 to 25 pounds-per-square inch gauge (psig).

In certain embodiments, the channel or series of channels connecting the inlet to the sample chamber has a width of from 0.2 to 1.0 mm, 0.4 to 0.8 mm, or 0.5 to 0.7 mm, and a depth of from 0.2 to 1.0 mm, 0.3 to 0.6 mm, or 0.3 to 0.5 mm. The channel may be formed at a depth such that it does not extend through the entire thickness of the core layer or it may be formed to extend through the entire thickness of the core layer. In embodiments where the channel depth extends through the entire thickness of the core layer, then the space within the channel is defined by the core layer, the first film, and the second film. In embodiments where the channel depth is formed only on one major face of the core layer (and has a depth less than the thickness of the core layer), then the space within the channel is defined by the core layer and the film bound to the major face on which the channel is located.

The sample chamber and air spring chamber may have a width and/or depth greater than that of the channel to which it is connected. In some embodiments, the sample chamber has a width of from 1 to 3 mm or from 1 to 2 mm, and a depth of from 0.5 to 3 mm, 0.5 to 2 mm, or 0.75 to 1.5 mm. In some embodiments, the air spring chamber has a width of from 1 to 3 mm or from 1 to 2 mm, and a depth of from 0.5 to 3 mm, 0.5 to 2 mm, or 0.75 to 1.5 mm. In certain embodiments, the length of the sample chamber is greater than its width or depth. In certain embodiments, the length of the air spring chamber is greater than its width or depth.

In some embodiments, the channel branches at least once such that the inlet is in fluid communication with at least two volumes, with each volume comprising a sample chamber and an air spring chamber. In one embodiment, the channel comprises three branches and four sample chambers. In another embodiment, the channel comprises seven branches and eight reaction volumes.

In one embodiment, the sample module comprises an inlet in one of the thermoplastic layers through which a sample can be introduced into a channel disposed between the two layers, and the channel is in fluid communication with at least one sample chamber and air spring chamber. The sample modules can be configured to handle microliter volumes of sample fluid. For example, the sample module can be configured such that each reaction volume contains from about 5 to 50 µl or 5 to 15 µl of the sample fluid.

Another embodiment of the invention provides a method of making a sample module, the method comprising: (a) injection molding a thermoplastic polymer to form a core layer having (i) a first major face and a second major face, wherein the first major face and the second major face are on opposite sides of the core layer; (ii) at least one cut out that extends through the thickness of the core layer from the first major face to the second major face; (iii) at least one channel formed in the first major face of the core layer; (b) bonding a first film to the first major face, wherein the first film covers the at least one cut out and the at least one channel; (c) bonding a second film to the second major surface of the core layer, wherein the second film covers the at least one cut out and, if the at least one channel extends through the entire thickness of the core layer, also covers the at least one channel; and (d) forming an inlet extending through the thickness of the first film, wherein the inlet may be formed prior to or after the first film is bonded to the first major face of the core layer.

That apparatus for thermal cycling may also be configured to detect signals, such as electromagnetic radiation, from the sample in the sample module. In one embodiment, the apparatus comprises a detection module configured to detect electromagnetic radiation emitted from the sample module. In certain embodiments, the apparatus comprises an illumination module configured to emit electromagnetic radiation toward the sample module. The detection module may be mounted on, for example, a retaining member or a thermal mass (e.g., the first thermal mass, the second thermal mass, the third thermal mass or the fourth thermal mass). The illumination module may be mounted on, for example, a retaining member or a thermal mass (e.g., the first thermal mass, the second thermal mass, the third thermal mass or the fourth thermal mass). In one embodiment, the detection module is mounted on a retaining member and the illumination module is mounted on a thermal mass. In yet another embodiment, both the detection module and the illumination module are mounted on the same thermal mass. In another embodiment, the detection module and the illumination module are mounted on opposing thermal masses, which contact the sample module at the same time (e.g., the second thermal mass and the fourth thermal mass). In still other embodiments, the detection module and/or the illumination module are mounted directly to the frame of the apparatus, and electromagnetic radiation is transmitted between the sample module and the detection module and/or the illumination module via one or more waveguides, such as an optical fiber.

In one embodiment, the retaining member comprises an illumination module and a detection module; the illumination module is configured to emit an excitation signal into each sample chamber and parallel to the length of each sample chamber of one or a plurality of sample chambers; and the detection module is configured to detect a response signal parallel to the length of each sample chamber of the one or plurality of sample chambers. In another embodiment, a thermal mass comprises an illumination module; the retaining element comprises a detection module; the illumination module is configured to emit an excitation signal into each sample chamber and perpendicular to the length of each sample chamber of one or a plurality of sample chambers; and the detection module is configured to detect a response signal parallel to the length of each sample chamber of the one or plurality of sample chambers. In certain embodiments, the illumination module may comprise a plurality of illumination elements, and wherein each illumination element is configured to illuminate a different sample chamber of the plurality of sample chambers. In a particular embodiment, an illumination element comprises one or more light emitting diodes (LEDs). In another embodiment, an illumination element comprises a laser. A detection module may comprise, for example, a charge coupled device (CCD), a complementary metal-oxide-semiconductor (CMOS), or a Silicon Photomultiplier (SiPM).

The components of the various embodiments of the apparatus disclosed herein may be enclosed in a housing. The housing may be ventilated to reduce the build-up of heat within the housing during use of the apparatus. In particular embodiments, the apparatus comprises one or more fans mounted to the housing or a frame of the apparatus, and configured to circulate air from outside the housing through at least a portion of the interior of the housing. In one embodiment, the apparatus comprises: a first fan coupled to the housing; a second fan coupled to the housing, wherein: the first fan is configured to direct air from outside the housing toward the second thermal mass when the first pivot arm is in the first position; and the second fan is configured to direct air from outside the housing toward the fourth thermal mass when the second pivot arm is in the first position.

In particular embodiments, the apparatus is compact and portable having external dimensions of the housing being no more than 12 inches×12 inches×12 inches, or 8 inches×8 inches×8 inches, or 6 inches×6 inches×6 inches, or 6 inches×4 inches×4 inches.

The various embodiments of the apparatus described herein can be used to perform thermal cycling. In particular embodiments, the apparatus is used in conjunction with a sample module as disclosed herein to perform thermal cycling. In one embodiment, for example, a method of thermal cycling a sample in a polymerase chain reaction is provided, the method comprising: retaining a sample module in a retaining member, wherein the sample module comprises a first major face and a second major face; pivoting a first pivot arm comprising a first thermal mass and a second thermal mass such that the first thermal mass contacts the first major face of the sample module; pivoting a second pivot arm comprising a third thermal mass and a fourth thermal mass such that the third thermal mass contacts the second major face of the sample module while the first thermal mass contacts the first major face of the sample module; pivoting the first pivot arm such that the second thermal mass contacts the first major face of the sample module; and pivoting the second pivot arm such that the fourth thermal mass contacts the second major face of the sample module while the second thermal mass contacts the first major face of the sample module.

The pivoting of the pivot arms may be repeated a plurality of times to thermal cycle the sample module between different temperatures a plurality of times. Such thermal cycling may be useful in applications such as performing PCR. In certain embodiments, the method is used to perform PCR at a rate of from 1 to 6 seconds per cycle, 2 to 5 seconds per cycle, or 3 to 5 seconds per cycle. One PCR cycle refers to the steps of DNA denaturation, primer annealing, and primer extension. The times referenced above (e.g., 1 to 6 seconds) refers to the time peak-to-peak, i.e., the time from one temperature peak of the sample module (or sample contained in the sample module) to the next temperature peak of the sample module (or sample contained in the sample module). In some embodiments, the heating thermal masses (e.g., the first and third thermal masses) are in contact with the first and second major faces of the sample module for about 1.5 to 3.5 seconds per cycle or 2 to 3 seconds per cycle (although may be in contact for longer for an initial denaturation step). In some embodiments, the cooling thermal masses (e.g., the second and fourth thermal masses) are in contact with the first and second major faces of the sample module for about 1 to 3 seconds per cycle or 1.5 to 2.5 seconds per cycle (although may be in contact for longer at the end of cycling in order to, for example, cool the chip for safer handling upon removal).

In some embodiments, the method comprises increasing the amount of time the cooling thermal masses are in contact with the first and second major faces of the sample module in order to compensate for an increase in temperature of the cooling thermal masses over a series of thermal cycles. For example, in one embodiment the amount of time the cooling thermal masses are in contact with the first and second major faces of the sample module may be increased by from 2 to 200 milliseconds per cycle, 2 to 100 milliseconds per cycle, 2 to 50 milliseconds per cycle, 2 to 20 milliseconds per cycle, 2 to 15 milliseconds per cycle, or 5 to 10 milliseconds per cycle. By way of example, if the first cycle of a PCR is performed in about 4.2 seconds, of which the cooling thermal masses are in contact with the first and second major faces of the sample module for about 1.9 seconds, and then the time the cooling thermal masses are in contact with the first and second major faces of the sample module is increased by about 8 milliseconds in each successive cycle, then by the $50^{th}$ cycle the cycle is performed in about 4.6 seconds with a contact time of about 2.3 seconds between the cooling thermal masses and the sample module.

In certain embodiments, the first thermal mass and the third thermal mass are within a first temperature range; the second thermal mass and the fourth thermal mass are within a second temperature range; and the first temperature range is a higher temperature range than the second temperature range. In particular embodiments, the sample module contains a sample having a target denaturing temperature and a target annealing temperature; said first temperature range is above the target denaturing temperature; and said second temperature range is below the target annealing temperature. The first temperature range may be, for example, from 98° C. to 130° C., and the second temperature range may be, for example, from 15° C. to 40° C. In one embodiment, the sample module contains a sample having a target denaturing temperature and a target annealing temperature; the first temperature range is centered around the target denaturing temperature; and the second temperature range is centered around the target annealing temperature. In one embodiment, the sample module contains a sample having a target denaturing temperature and a target annealing temperature; the first temperature range is above the target denaturing temperature; and the second temperature range is below the target annealing temperature. In particular embodiments the first temperature range and the second temperature range each spans no more than 3° C., 2° C., 1° C., or 0.5° C. while the method of thermal cycling a sample in a polymerase chain reaction is performed.

In some embodiments, the thermal cycling method is performed using a sample module comprising a plurality of sample chambers. In particular embodiments, each sample chamber of the plurality of sample chambers has a length and a width, wherein the length is greater than the width. In one embodiment, the retaining member comprises an illumination module and a detection module, and the method for performing thermal cycling further comprises emitting an excitation signal from the illumination module, wherein the excitation signal is emitted parallel to the length of each sample chamber of the plurality of sample chambers; and the method further comprises detecting a response signal with the detection module, wherein the response signal is detected parallel to the length of each sample chamber of the plurality of sample chambers. In another embodiment, at least one thermal mass (e.g., the first thermal mass, the second thermal mass, the third thermal mass or the fourth thermal mass) comprises an illumination module and at least one thermal mass (e.g., the first thermal mass, the second thermal mass, the third thermal mass or the fourth thermal mass) comprises a detection module, and the method for performing thermal cycling further comprises emitting an excitation signal from the illumination module, wherein the excitation signal is emitted perpendicular to the length of each sample chamber of the plurality of sample chambers; and the method further comprises detecting a response signal with the detection module, wherein the response signal is detected perpendicular to the length of each sample chamber of the plurality of sample chambers. In certain aspects, the illumination module comprises a plurality of illumination elements, and wherein each illumination element is configured to illuminate a sample chamber of the plurality of sample chambers. The plurality of illumination elements may be, for example, light emitting diodes (LEDs) or lasers.

The pivot arms may be moved by one or more actuators. For example, in one embodiment, the first pivot arm is pivoted via a first actuator coupled to the first pivot arm; and the second pivot arm is pivoted via a second actuator coupled to the second pivot arm, wherein a controller is configured to actuate the first actuator and the second actuator. In some embodiments, both pivot arms are connected to the same actuator. The first pivot arm can pivot around a first pivot axis; and the second pivot arm can pivot around a second pivot axis; and the sample module may be retained between the first pivot axis and the second pivot axis.

The method may further comprise reducing a temperature of the second thermal mass and a temperature of the fourth thermal mass via at least one cooling element. In one embodiment, the cooling element is a fan or a plurality of fans. In another embodiment, the cooling element is a TEC. In yet another embodiment, the cooling element is not a TEC. In particular embodiments, the temperature of the second thermal mass is reduced via a first cooling element; and the temperature of the fourth thermal mass is reduced via a second cooling element. In one embodiment, a first fan is coupled to the housing and a second fan is coupled to the housing, and the method further comprises operating the first fan to direct air from outside the housing toward the second thermal mass when the first pivot arm is in the first position; operating the second fan to direct air from outside the housing toward the fourth thermal mass when the second pivot arm is in the first position. In some embodiments, the only active cooling element in the apparatus is a fan or a plurality of fans. In other embodiments, the apparatus uses only passive cooling to cool the thermal masses. Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

Although the invention has been described with respect to specific embodiments thereof, these embodiments are merely illustrative, and not restrictive of the invention. The description herein of illustrated embodiments of the invention, including the description in the Abstract and Summary, is not intended to be exhaustive or to limit the invention to the precise forms disclosed herein (and in particular, the inclusion of any particular embodiment, feature or function within the Abstract or Summary is not intended to limit the scope of the invention to such embodiment, feature or function). Rather, the description is intended to describe illustrative embodiments, features and functions in order to provide a person of ordinary skill in the art context to understand the invention without limiting the invention to any particularly described embodiment, feature or function, including any such embodiment feature or function described in the Abstract or Summary. While specific embodiments of, and examples for, the invention are described herein for illustrative purposes only, various equivalent modifications are possible within the spirit and scope of the invention, as those skilled in the relevant art will recognize and appreciate. As indicated, these modifications may be made to the invention in light of the foregoing description of illustrated embodiments of the invention and are to be included within the spirit and scope of the invention. Thus, while the invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the invention. The disclosures of all patents, patent applications and publications cited herein are hereby incorporated herein by reference in their entireties, to the extent that they are consistent with the present disclosure set forth herein.

Reference throughout this specification to "one embodiment", "an embodiment", or "a specific embodiment" or similar terminology means that a particular feature, structure, or characteristic described in connection with the embodiment is included in at least one embodiment and may not necessarily be present in all embodiments. Thus, respective appearances of the phrases "in one embodiment", "in an embodiment", or "in a specific embodiment" or similar terminology in various places throughout this specification are not necessarily referring to the same embodiment. Furthermore, the particular features, structures, or characteristics of any particular embodiment may be combined in any suitable manner with one or more other embodiments. It is to be understood that other variations and modifications of the embodiments described and illustrated herein are possible in light of the teachings herein and are to be considered as part of the spirit and scope of the invention.

In the description herein, numerous specific details are provided, such as examples of components and/or methods, to provide a thorough understanding of embodiments of the invention. One skilled in the relevant art will recognize, however, that an embodiment may be able to be practiced without one or more of the specific details, or with other apparatus, systems, assemblies, methods, components, materials, parts, and/or the like. In other instances, well-known structures, components, systems, materials, or operations are not specifically shown or described in detail to avoid obscuring aspects of embodiments of the invention. While the invention may be illustrated by using a particular embodiment, this is not and does not limit the invention to any particular embodiment and a person of ordinary skill in the art will recognize that additional embodiments are readily understandable and are a part of this invention.

At least a portion of embodiments discussed herein can be implemented using a computer communicatively coupled to a network (for example, the Internet), another computer, or in a standalone computer. As is known to those skilled in the art, a suitable computer can include a processor or central processing unit ("CPU"), at least one read-only memory ("ROM"), at least one random access memory ("RAM"), at least one hard drive ("HD"), and one or more input/output ("I/O") device(s). The I/O devices can include a keyboard, monitor, printer, electronic pointing device (for example, mouse, trackball, stylist, touch pad, etc.), or the like.

ROM, RAM, and HD are computer memories for storing computer-executable instructions executable by the CPU or capable of being complied or interpreted to be executable by the CPU. Suitable computer-executable instructions may reside on a computer readable medium (e.g., ROM, RAM, and/or HD), hardware circuitry or the like, or any combination thereof. Within this disclosure, the term "computer readable medium" is not limited to ROM, RAM, and HD and can include any type of data storage medium that can be read by a processor. For example, a computer-readable medium may refer to a data cartridge, a data backup magnetic tape, a floppy diskette, a flash memory drive, an optical data storage drive, a CD-ROM, ROM, RAM, HD, or the like. Software implementing some embodiments disclosed herein can include computer-executable instructions that may reside on a non-transitory computer readable medium (for example, a disk, CD-ROM, a memory, etc.). Alternatively, the computer-executable instructions may be stored as software code components on a direct access storage device array, magnetic tape, floppy diskette, optical storage device, or other appropriate computer-readable medium or storage device.

Any suitable programming language can be used to implement the routines, methods or programs of embodiments of the invention described herein, including the custom script. Other software/hardware/network architectures may be used. For example, the software tools and the custom script may be implemented on one computer or shared/distributed among two or more computers in or across a network. Communications between computers implementing embodiments can be accomplished using any electronic, optical, radio frequency signals, or other suitable methods and tools of communication in compliance with known network protocols. Additionally, any signal arrows in the drawings/figures should be considered only as exemplary, and not limiting, unless otherwise specifically noted. Based on the disclosure and teachings provided herein, a person of ordinary skill in the art will appreciate other ways and/or methods to implement the invention.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" or "approximately" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, process, article, or apparatus.

Furthermore, the term "or" as used herein is generally intended to mean "and/or" unless otherwise indicated. For example, a condition A or B is satisfied by any one of the following: A is true (or present) and B is false (or not present), A is false (or not present) and B is true (or present), and both A and B are true (or present). As used herein, including the claims that follow, a term preceded by "a" or "an" (and "the" when antecedent basis is "a" or "an") includes both singular and plural of such term, unless clearly indicated within the claim otherwise (i.e., that the reference "a" or "an" clearly indicates only the singular or only the plural). Also, as used in the description herein, the meaning of "in" includes "in" and "on" unless the context clearly dictates otherwise.

As used herein, "patient" or "subject" includes mammalian organisms, such as human and non-human mammals, for example, but not limited to, rodents, mice, rats, non-human primates, companion animals such as dogs and cats as well as livestock, e.g., sheep, cow, horse, etc. Therefore, for example, although the described embodiments illustrate use of the present methods on humans, those of skill in the art would readily recognize that these methods and compositions could also be applied to veterinary medicine as well as on other mammals.

DETAILED DESCRIPTION OF THE INVENTION

Exemplary embodiments of the present disclosure include apparatus and methods for polymerase chain reaction (PCR) thermal cycling. Particular embodiments are discussed below with reference to the drawings included in the figures.

Figure 1:
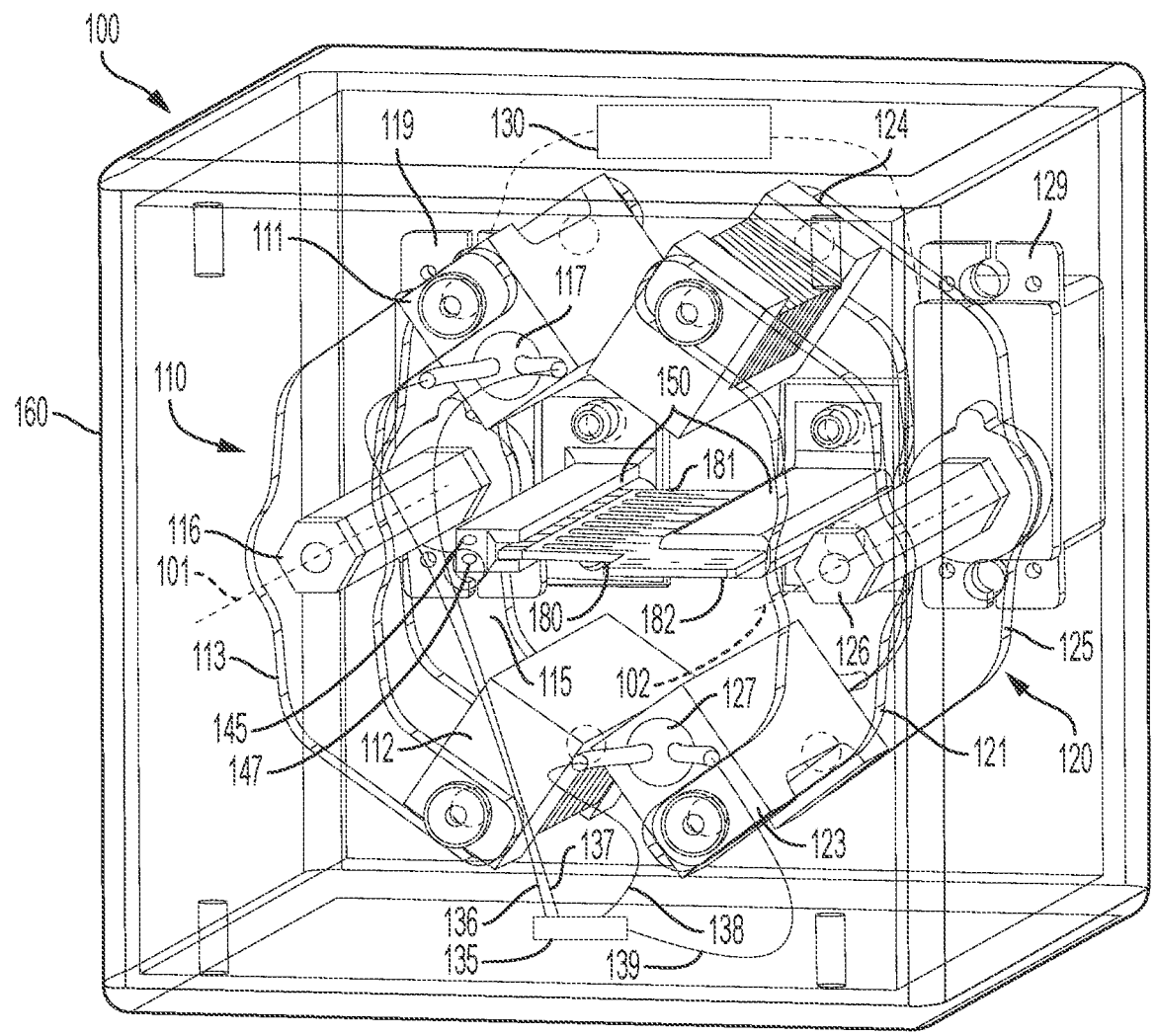
FIG. 1 is a perspective view of an apparatus according to a first exemplary embodiment of the present disclosure.
Figure 2:
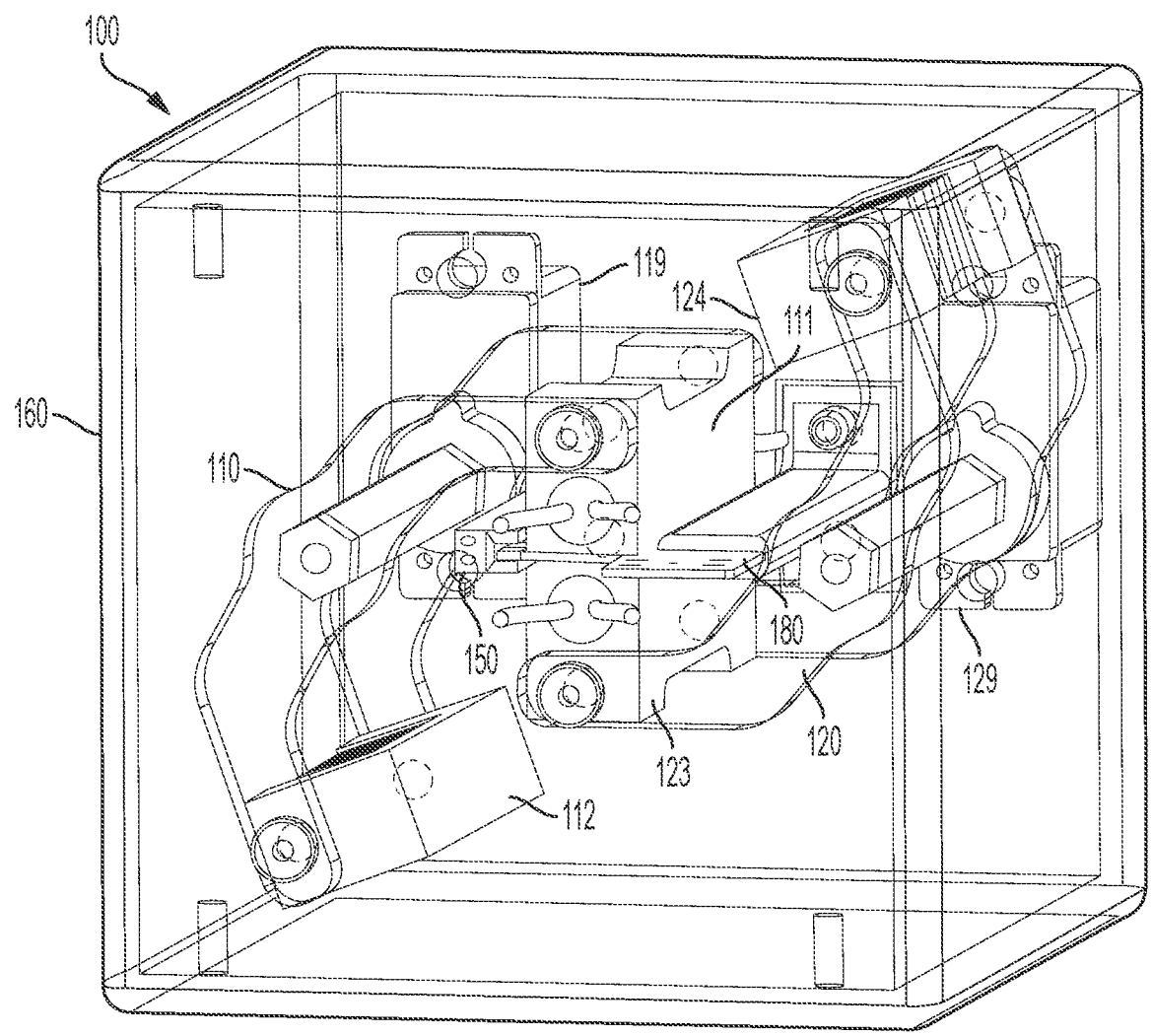
FIG. 2 is a perspective view of the embodiment of FIG. 1 in a first position.
Figure 3:
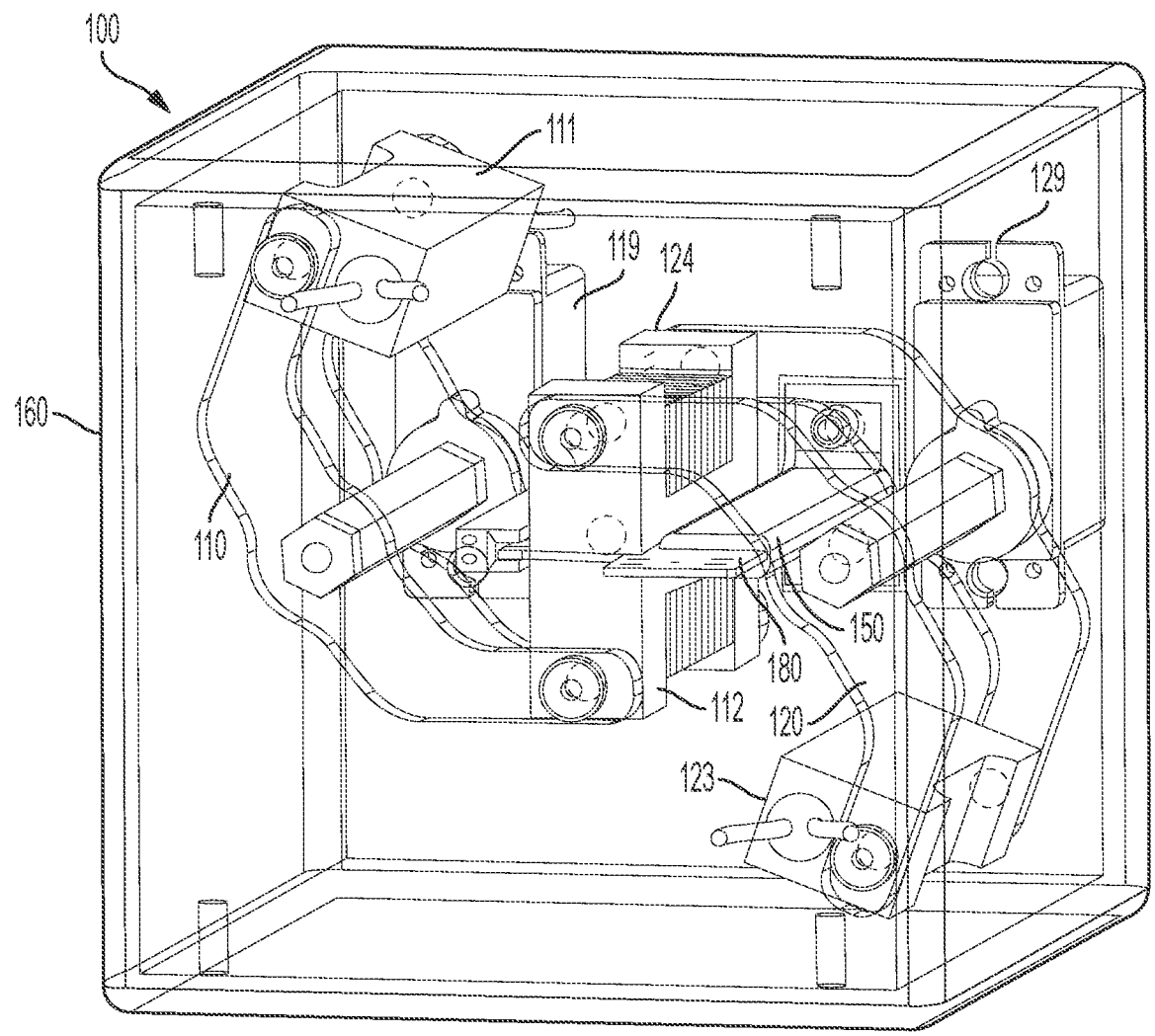
FIG. 3 is a perspective view of the embodiment of FIG. 1 in a second position.

Referring initially to FIGS. 1-3, an apparatus 100 for thermal cycling is shown comprising a housing 160 with a retaining member 150 coupled to housing 160. In the embodiment shown, retaining member 150 is configured to retain a sample module 180. In particular embodiments, sample module 180 may comprise one or more sample chambers suitable for use in a polymerase chain reaction (PCR) process. In certain embodiments, sample module 180 is a separate component from apparatus 100 that can be inserted and removed from retaining member 150, and sample module 180 is shown in the figures for illustration of operational aspects of apparatus 100. For purposes of clarity, not all components illustrated in the figures are labeled with reference numbers. It is also understood that the components shown in FIGS. 2 and 3 that are not labeled are equivalent to those labeled in FIG. 1. Certain components included in the view of FIG. 1 are also not shown in FIGS. 2 and 3 for purposes of clarity. It is understood that the embodiment shown in FIGS. 2 and 3 includes each of the components shown in FIG. 1.

In the illustrated embodiment, apparatus 100 further comprises a first pivot arm 110 configured to pivot around a first pivot axis 101 and a second pivot arm 120 configured to pivot around a second pivot axis 102. In the embodiment shown, apparatus 100 also comprises a first thermal mass 111 and a second thermal mass 112 each coupled to first pivot arm 110, as well as a third thermal mass 123 and a fourth thermal mass 124 each coupled to second pivot arm 120. In particular embodiments, thermal masses 111, 112, 123 and 124 may comprise material with a high coefficient of thermal conductivity. In specific embodiments, thermal masses 111, 112, 123 and 124 may comprise copper or aluminum blocks of material.

First arm 110 and second arm 120 are shown in a first position in FIG. 2 and in a second position in FIG. 3. In FIG. 1, first arm 110 and second arm 120 are shown in an intermediate position between the first and second positions. First thermal mass 111 and third thermal mass 123 are proximal to the retaining member when first pivot arm 110 and the second pivot arm 120 are in the first position shown in FIG. 2. In addition, second thermal mass 112 and the fourth thermal mass 124 are proximal to retaining member 150 when first pivot arm 110 and second pivot arm 120 are in the second position shown in FIG. 3.

As shown in FIG. 1, sample module 180 comprises a first side 181 (e.g. the top side in the orientation shown) and a second side 182 (e.g. the bottom side in the orientation shown). When sample module 180 is retained in retaining member 150, first and second pivot arms 110 and 120 can pivot between the first and second position such that certain thermal masses 111, 112, 123 and 124 alternately contact the first side 181 and second side 182 of sample module 180. In the illustrated embodiment shown, first thermal mass 111 is in contact with first side 181 and third thermal mass 123 is in contact with second side 182 when first pivot arm 110 and second pivot arm 120 are in the first position shown in FIG. 2. In addition, second thermal mass 112 is in contact with second side 182 and the fourth thermal mass 124 is in contact with the first side 181 when first pivot arm 110 and second pivot arm 120 are in the second position shown in FIG. 3.

In the embodiment shown, first thermal mass 111 comprises a heating element 117 and third thermal mass 123 comprises a heating element 127. In certain embodiments, heating elements 117 and 127 are electrically coupled to a power source 135 via wires 136, 137, 138 and 139 that have sufficient length for to allow first and second pivot arms 110, 120 to pivot from the first position to the second position while remaining electrically coupled to power source 135. During operation of apparatus 100, heating elements 117 and 127 can increase the temperature of first thermal mass 111 and third thermal mass 123. In the embodiment shown, second thermal mass 112 and fourth thermal mass 124 do not include heating elements. Accordingly, heating elements 117 and 127 can be activated to increase the temperature range of first thermal mass 111 and third thermal mass 123 to a temperature range that is higher than the temperature range of second thermal mass 112 and fourth thermal mass 124.

In specific embodiments, first thermal mass 111 and third thermal mass 123 are maintained at a temperature range at or above the denaturing temperature of the target oligomer(s), and second thermal mass 112 and fourth thermal mass 124 are maintained at or below the annealing temperature of the target oligomer(s). The first thermal mass 111 and the third thermal mass 123 could therefore be referred to as heating masses, and the second thermal mass 112 and the fourth thermal mass 124 could be referred to as cooling masses. During operation of apparatus 100, first and second arms 110 and 120 can pivot from the first position shown in FIG. 2 to the second position shown in FIG. 3 to cycle the temperature of the contents of sample module 180 from a higher temperature to a lower temperature as used in PCR processes.

The heating masses and cooling masses can be used in at least two major modes of operation—a steady-state mode or a transient mode. In a steady-state mode, the heating masses are set to the denaturing temperature, and the cooling masses are set to the annealing temperature. Alternatively, the heating masses can be set to a temperature with a range centered around the denaturing temperature, and the cooling masses can be set to begin at a temperature within a range centered around the annealing temperature. During the denaturing phase, the heating masses remain clamped around the sample module 180 until the temperature of the fluid in the sample chambers 18 reaches or substantially reaches the temperature of the heating masses. During the annealing phase, the cooling masses remain clamped around the sample module 180 until the temperature of the fluid in the sample chambers 18 reaches or substantially reaches the temperature of the cooling masses. In steady-state mode, the heating masses could be maintained at a constant temperature within a temperature range such as 85-98 C, or 90-98 C, or even 94-98 C. The cooling masses could be maintained within the range of 50-70 C, or 55-65 C, or 58-62 C. These ranges are merely illustrative, as the desired temperatures may vary depending on the assay.

In a transient mode of operation (or alternatively called overshoot mode), the heating and cooling masses are set to temperatures that overshoot the desired denature and anneal temperatures, and they contact the sample module 180 for only enough time for the fluid in the sample chambers 18 to reach the desired denaturing or annealing temperatures. For example, the heating masses could be set to maintain a steady temperature of 120 Celsius, and the cooling masses could begin at room temperature, around 24 Celsius. The sample module 180 and fluid within the sample chambers 183-190 might also begin at or near room temperature. Even though the heating masses are at 120 Celsius, they contact the sample module 180 only for sufficient time for the fluid within the sample chambers 183-190 to reach the desired denaturing temperature, e.g. 95 Celsius. Similarly, the cooling masses contact the sample module 180 only for enough time for the fluid within the sample chambers 183-190 to reach the desired annealing temperature, e.g. 60 C. In one embodiment, the time required for fluid within the sample chambers 183-190 to increase in temperature from 60 to 95 Celsius ranges from a couple to several seconds, and the time required for the fluid within the sample chambers 183-190 to decrease from 95 to 60 Celsius ranges from one to several seconds. The heating masses can be maintained at a steady temperature within the range of 98-130 C, 110-130 C, or 115-125 C. The cooling masses can begin thermal-cycling at a temperature within the range of 15-40 C, 20-30 C, or 20-25 C.

Note, however, that the denaturing and annealing temperatures can be dictated by the chemistry and assay requirements, and the contacting times for heating and cooling may be adjusted accordingly. For example, instead of a 35-Celsius cycling delta (difference between 95 Celsius and 60 Celsius), a smaller cycling delta might be preferred. A 20-Celsius delta might be seen by cycling between denaturing and annealing temperatures of 85 Celsius and 65 Celsius. An even smaller cycling delta might be seen by cycling, for example, from around 70 Celsius to mid-80's Celsius.

In the embodiment shown, apparatus 100 comprises a controller 130 configured to control apparatus 100 including the movement of first pivot arm 110 and second pivot arm 120 between the first position and second positions. For example, controller 130 can actuate a first actuator 119 coupled to first pivot arm 110 and actuate a second actuator coupled 129 to second pivot arm 120. In other embodiments, controller 130 may actuate a single actuator that is coupled to both first pivot arm 110 and second pivot arm 120 via a belt, gear, or other suitable configuration.

In certain embodiments, controller 130 is configured to maintain first pivot arm 110 and second pivot arm 120 in the first position for a specific period of time and maintain first pivot arm 110 and second pivot arm 120 in the second position for a different period of time. In some embodiments, controller 130 is configured to maintain first pivot arm 110 and second pivot arm 120 in the first position for an initial time period, and then alternate first pivot arm 110 and second pivot arm 120 between the first and second position for different time periods. For example, controller 130 can maintain first pivot arm 110 and second pivot arm 120 in the first position for an initial period of several minutes and then alternate first pivot arm 110 and second pivot arm 120 between the first and second positions for periods of time at each position ranging from about a second to several seconds.

In certain embodiments, apparatus 100 comprises an illumination module 145 configured to illuminate contents of sample module 180 retained by the retaining member 150. Apparatus 150 may further comprise a detection module 147 configured to detect contents of sample module 180 illuminated by illumination module 145. In certain embodiments, detection module 147 is configured to detect contents of sample module 180 that fluoresce in response to excitation energy provided by illumination module 145. In the illustrated embodiment, retaining member 150 comprises illumination module 145 and detection module 147. The location of illumination module 145 and detection module 147 shown is for illustrative purposes only, and in other embodiments retaining member 150 may comprise different locations for illumination module 145 and detection module 147 (e.g. above and below sample module 180, or both proximal to one end of sample module 180, etc.). In other embodiments, other components of apparatus 100 may comprise an illumination module and a detection module. For example, first thermal mass 111, second thermal mass 112, third thermal mass 123 and/or fourth thermal mass 124 may comprise an illumination module and/or a detection module. In certain embodiments, illumination module 145 may comprise light-emitting diodes (LEDs) or lasers emitting light at different frequencies. In particular embodiments, detection module 147 may comprise photodetectors or other light-sensing elements. In specific embodiments, apparatus 100 may comprise fiber-optic elements in communication with detection module 147.

During operation, apparatus 100 provides efficient thermal cycling of sample module 180. For example, the ability to provide heat transfer simultaneously to both first side 181 and second side 182 can increase the heat transfer rate to the contents of sample module 180 as compared to systems that provide heat transfer to only one side of a sample module 180. Contacting each side of sample module 180 with first and third thermal masses 111, 123, for example, transfers heat through more of the available surface area of the sample module 180 compared to single-sided heating systems. This can reduce the amount of time needed to bring the contents of sample module 180 to the desired temperature during a cycle. Certain sample processing techniques require a significant number of cycles (e.g. 50-100), so reducing the time for a single cycle can have a substantial reduction in the overall processing time.

Similarly, engaging both sides of sample module 180 with second and fourth thermal masses 112, 124 can reduce the amount of time needed to lower the temperature of sample module 180 to the desired temperature range. The increased surface area contacted by second and fourth thermal masses 112, 124 (as compared to single sided contact embodiments) can also reduce the amount of time required for each thermal cycle.

In the embodiment shown, first pivot arm 110 is shown comprising a first bracket arm 113 and a second bracket arm 115 with a spacer bar 116 extending between them. Similarly, second pivot arm 120 is shown comprising a first bracket arm 121 and a second bracket arm 125 with a spacer bar 126 extending between them. For discussion purposes, first pivot arm 110 includes first bracket arm 113, second bracket arm 115 and spacer bar 116, while second pivot arm 120 includes first bracket arm 121, second bracket arm 125 and spacer bar 126. It is understood that other embodiments may comprise a different configuration for first and second pivot arms 110, 120, including for example, single arms for each pivot arm.

Figure 4:
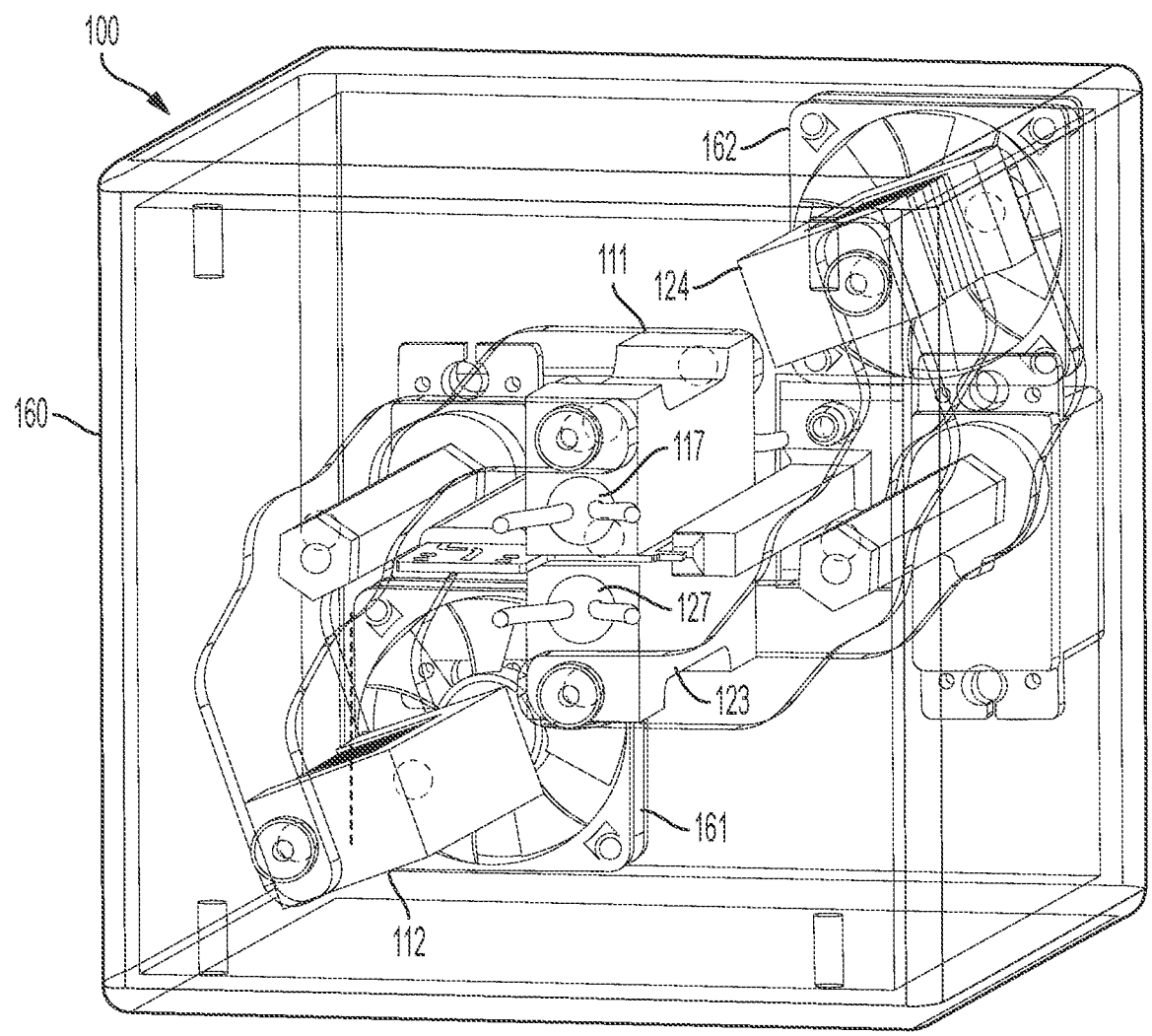
FIG. 4 is perspective view of the embodiment of FIG. 1 with additional components.

Referring now to FIG. 4, an embodiment of apparatus 100 is shown that is equivalent to the embodiment shown in FIGS. 1-3, but also includes cooling elements 161 and 162. In certain embodiments, cooling elements 161 and 162 may be configured as electric fans configured to direct air from outside housing 160 into housing 160. For purposes of clarity, not all components illustrated in FIG. 4 are labeled with reference numbers. It is understood that the components shown in FIG. 4 operate in a manner equivalent to those previously discussed with respect to FIGS. 1-3.

As previously discussed, during operation of apparatus 100, heating elements 117 and 127 heat first and third thermal masses 111, 123 which transfer the heat to sample module 180. As a result of the heat generated by heating elements 117 and 127 and transferred to other components of apparatus 100, the temperature within housing 160 can become elevated. As a result, the temperature of second and fourth thermal masses 112, 124 can also increase over time. Cooling elements 161 and 162 are positioned within housing 160 such that they direct air from outside housing 160 toward second thermal mass 112 and fourth thermal mass 124 when first and second pivot arms 110, 120 are in the first position (i.e. second thermal mass 112 and fourth thermal mass 124 are not in contact with sample module 180). The air from outside housing 160 will typically be a lower temperature than the air within housing 160 during operation of apparatus 100. The air from outside housing 160 will also typically be a lower temperature than the temperature of second thermal mass 112 and fourth thermal mass 124. Accordingly, cooling elements 161 and 162 can direct air to second thermal mass 112 and fourth thermal mass 124 that reduces the temperature of second thermal mass 112 and fourth thermal mass 124, for example, by convective heat transfer. In certain embodiments, apparatus 100 may comprise one or more vents 163 to increase air flow within housing 160 and reduce the temperature increase within housing 160 during operation of apparatus 100. If desired, the vents 163 can be located on the wall opposite that with the cooling elements 161 and 162 such that cooler external air tends to interact with and flow past the cooling second and fourth thermal masses 112 and 124 more than the heating first and third thermal masses 111 and 123. In certain embodiments, vent 163 may comprise a fan configured to evacuate air from within housing 160.

Figure 5:
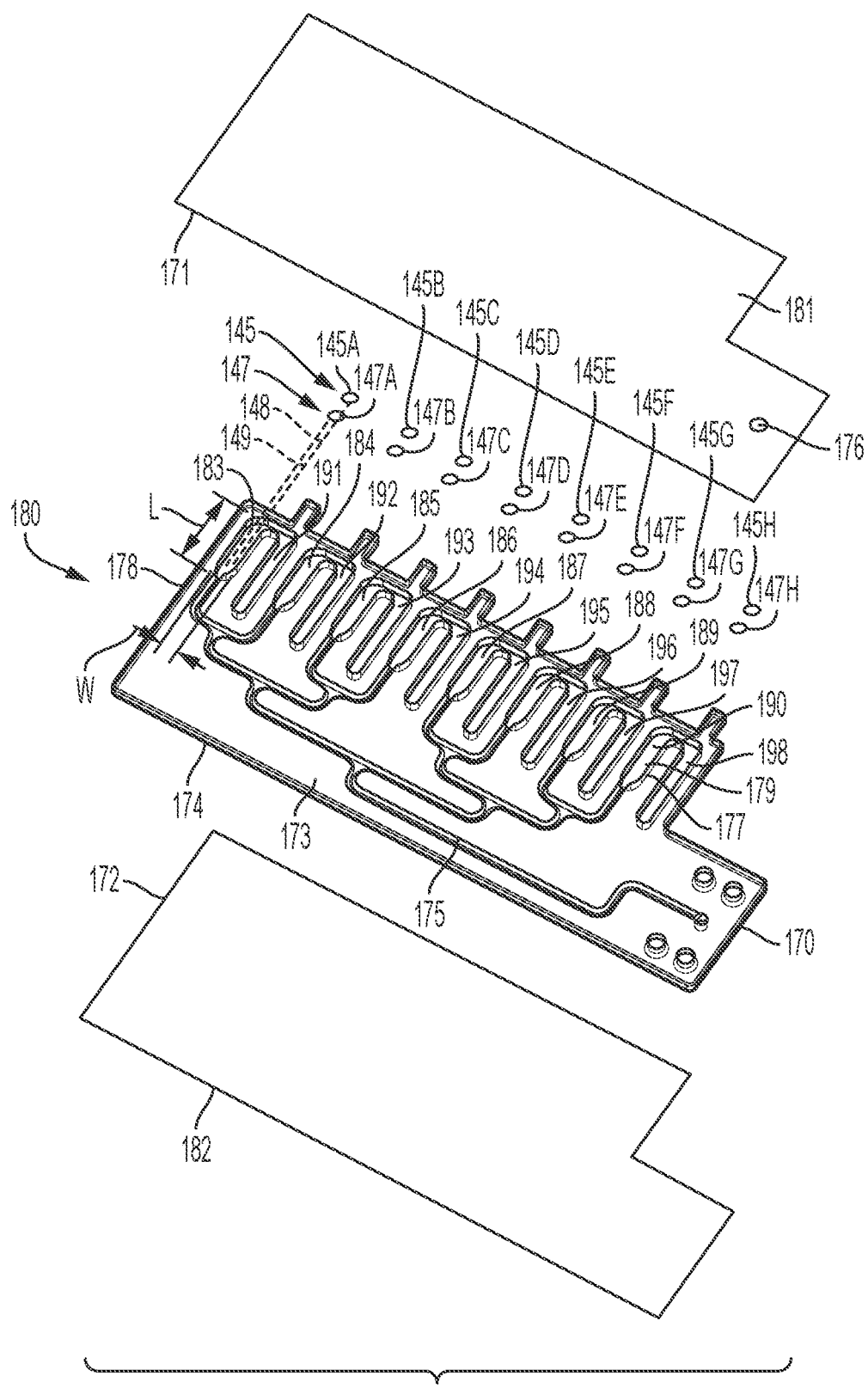
FIG. 5 is a perspective view of components for use in conjunction with the embodiment of FIG. 1.

Referring now to FIG. 5, an embodiment of sample module 180 is shown in an exploded view. In certain embodiments, sample module 180 may be formed by heat-sealing biaxially oriented polypropylene film (BOPP) to a polypropylene base material. In the embodiment shown, sample module 180 comprises a core layer 170 that is generally planar and comprises a first major face 173, a second major face 174 and an outer edge 178. Sample module 180 further comprises a first film 171 bonded to first major face 173 and a second film 172 bonded to second major face 174 of a core layer 170. In the embodiment shown, sample module 180 comprises first side 181 on first film 171 and second side 182 on second film 172.

In addition, sample module 180 comprises an inlet 176, channel 175 and multiple sample chambers 183-190 in fluid communication with corresponding air spring chambers 191-198. In the embodiment shown, inlet 176 extends through the thickness of first film 171, while channel 175 is formed in the first major face 173 (but does not extend through to the second major face 174), and sample chambers 183-190 and air spring chambers 191-198 are formed by cutting out portions of core layer 170. Core layer 170 comprises an inner edge 177 that extends along sample chambers 183-190 and air spring chambers 191-198. Inner edge 177, first film 171 and second film 172 define a volume 179 for sample chambers 183-190 and air spring chambers 191-198. First film 171 and core layer 170 define channel 175.

Air spring chambers 191-198 can be configured such that fluid can flow from sample chambers 183-190 to the corresponding air spring chamber 191-198. In certain embodiments, air spring chambers 191-198 can be sized and configured such that the pressure within sample chambers 183-190 and air spring chambers 191-198 is approximately 20 pounds-per-square inch gauge (psig) as fluid begins to flow from a sample chamber to an air spring chamber—at which point all of the air within the previously empty chip has been compressed into the air spring chambers 191-198. In the embodiment shown, sample chambers 183-190 are configured such that the length L of each sample chamber 183-190 is greater than the width W of each sample chamber 183-190.

Figure 11:
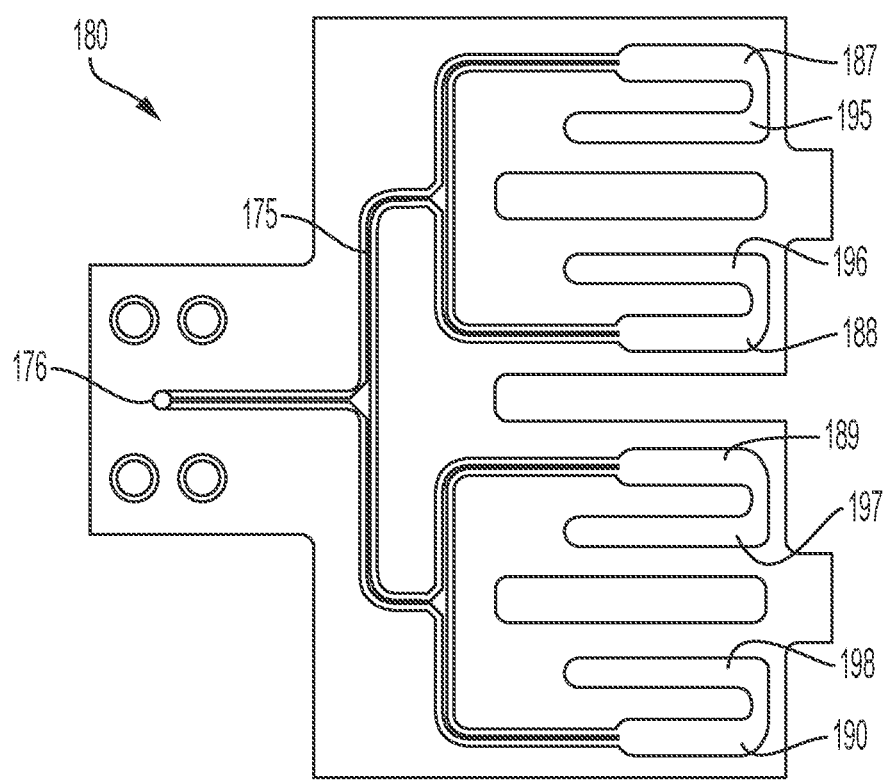
FIG. 11 is a top view of a sample module according to a first exemplary embodiment of the present disclosure prior to the introduction of sample fluid.
Figure 12:
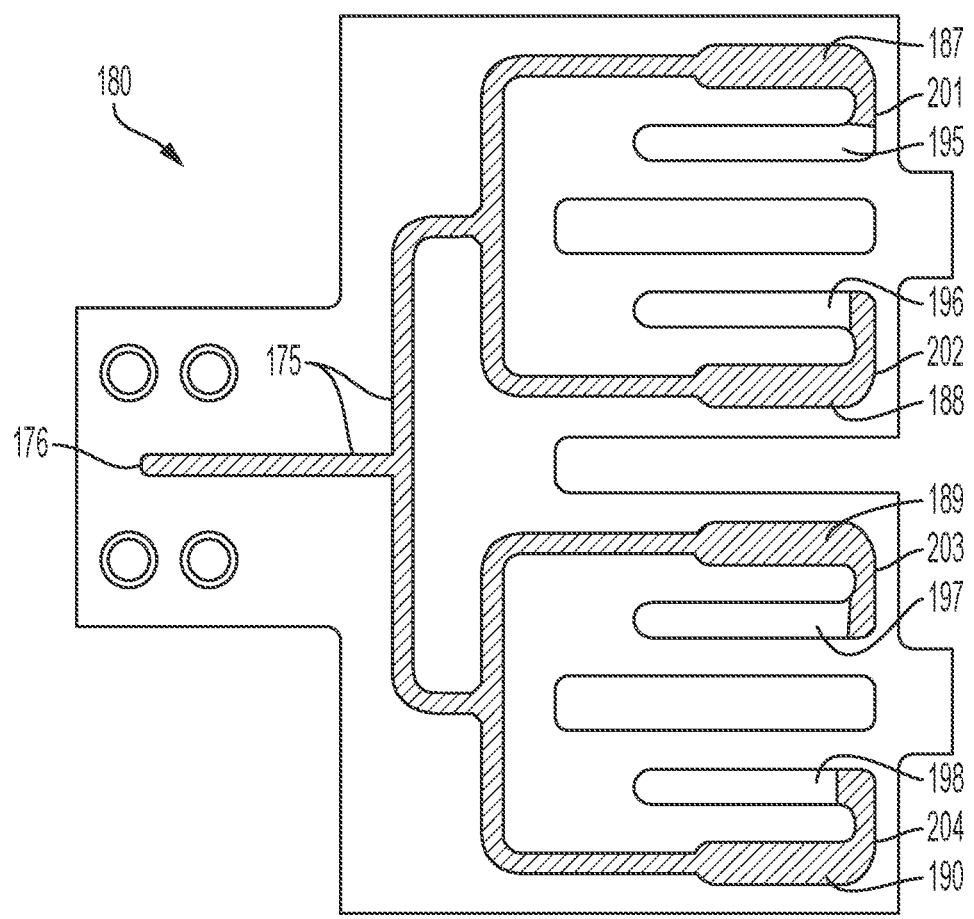
FIG. 12 is a top view of the embodiment of FIG. 11 after the introduction of sample fluid.

FIGS. 11 and 12 further illustrate aspects of air spring chambers and sample chambers. In the embodiment shown, sample module 180 comprises inlet 176, channel 175, sample chambers 187-190 and air spring chambers 195-198. FIG. 11 illustrates sample module 180 before fluid enters, while FIG. 12 illustrates sample module 180 after sample fluid 199 enters sample chambers 187-190 via inlet 176 and channel 175.

As shown in FIG. 12, when sample fluid 199 is loaded into sample module 180, sample fluid 199 fills sample chambers 187-190. Air displaced from sample chambers 187-190 by sample fluid 199 is compressed in air spring chambers 195-198. As previously discussed, the U-shaped configuration of sample chambers 187-190 and air spring chambers 195-198 permit optical excitation and detection of labeled analytes through end portions 201-204 that contain sample fluid 199. In particular embodiments, at least half of the total empty air volume in sample chambers 187-190 is compressed into air spring chambers 195-198 once sample fluid 199 is loaded onto sample module 180.

In the embodiment shown in FIG. 12, sample fluid 199 can be introduced into sample module 180 via inlet 176 and channel 175. Sample fluid 199 can then be transferred to sample chambers 187-190 by applying pressure via inlet 176. The air displaced from channel 175 and sample chambers 187-190 can then be compressed in air spring chambers 195-198. In certain embodiments, air is compressed in air spring chambers 195-198 from 5 to 50 pounds-per-square inch gauge (psig), 10 to 30 pounds-per-square inch gauge (psig), or 15 to 25 pounds-per-square inch gauge (psig).

In the embodiment of FIG. 5, illumination module 145 comprises a plurality of illumination elements 145A-145H configured to illuminate sample chambers 183-190, respectively. In certain embodiments, illumination elements 145A-145H may be individual light emitting diodes (LEDs) or lasers. In addition, detection module 147 comprises detection elements 147A-147H configured to detect a response signal (e.g. a fluorescent signal resulting from illumination by illumination elements 145A-145H) from sample chambers 183-190, respectively. In the embodiment shown, illumination elements 145A-145H are configured to illuminate sample chambers 183-190 along the length L of sample chambers 183-190. Similarly, detection elements 147A-147H configured to detect a response along the length L of sample chambers 183-190. As illustrated in FIG. 5, illumination element 145A is shown illuminating sample chamber 183 with an excitation signal 148 and detection element 147A is shown detecting a response signal 149 from sample chamber 183. As shown, excitation signal 148 and response signal 149 are emitted and detected in a direction parallel to the length (e.g. the largest dimension of sample chamber 183). Such a configuration can be beneficial in detecting a response signal from a small volume contained within the sample chamber. It is understood that illumination elements 145B-145H and detection elements 147B-147H are configured equivalent to illumination element 145A and detection element 147A, respectively. Accordingly, illumination module 145 and detection module 147 can provide excitation signals and detect response signals to a plurality of sample chambers on a single sample module 180. In certain embodiments, illumination elements 145A-145H can emit excitation signals with different wavelengths and/or detection elements 147A-147H can detect signals of different wavelengths. In particular embodiments, sample chambers 183-190 may comprise different reagents that react with different target analytes to provide different response signals. Accordingly, a single sample can be loaded into sample module 180 and simultaneously analyzed for multiple target analytes.

Figure 6:
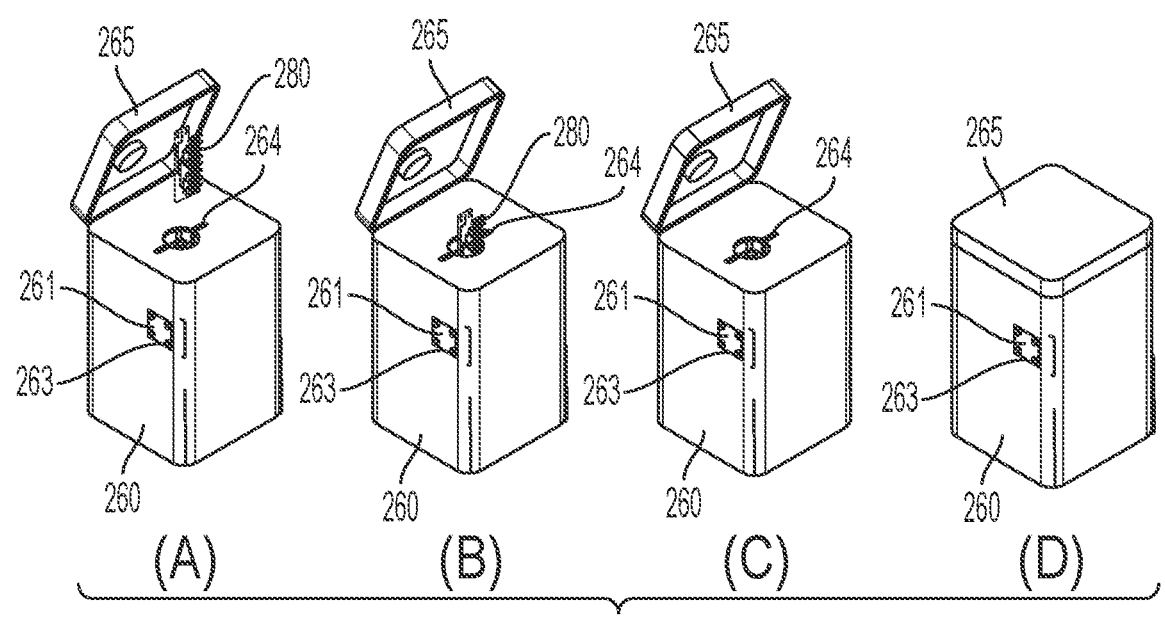
FIG. 6 is a second exemplary embodiment of the present disclosure, with the sample module and lid shown in various positions in views A-D.
Figure 7:
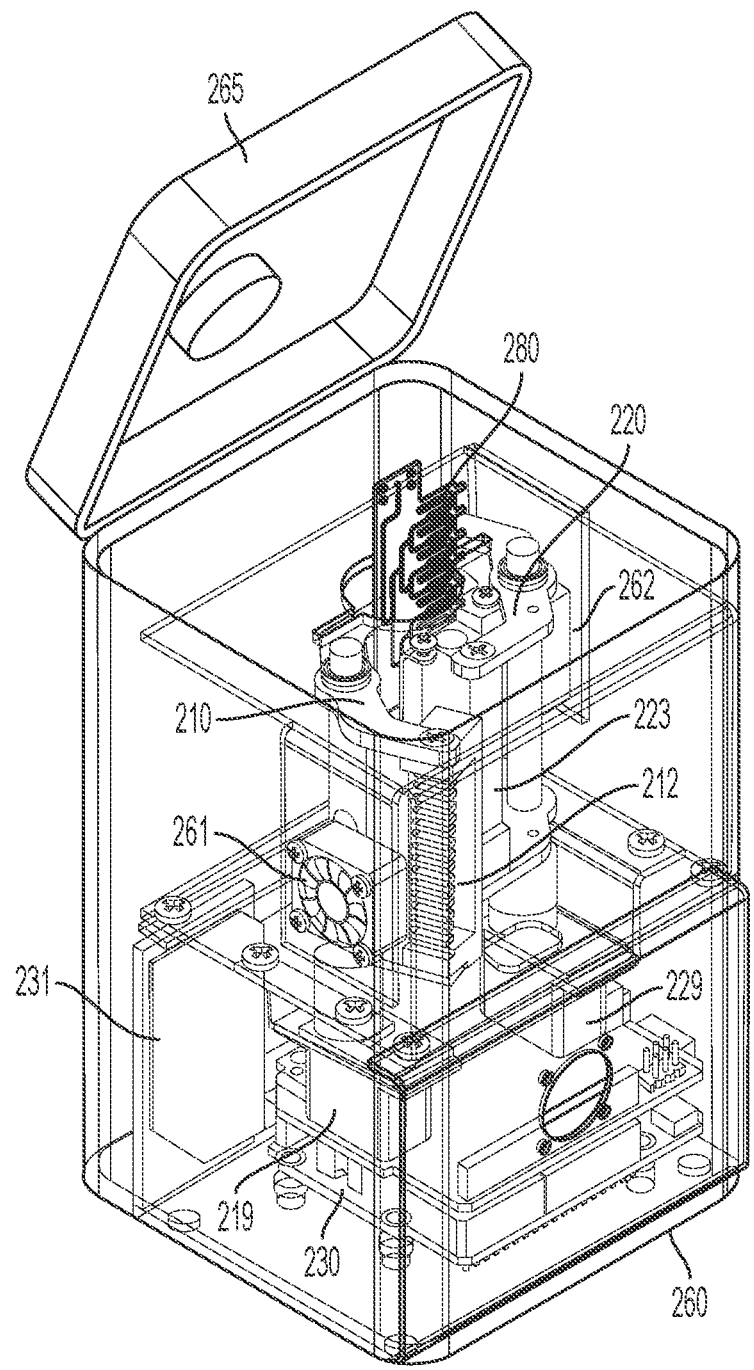
FIG. 7 is a perspective view of the embodiment of FIG. 6 with portions of the housing made transparent so elements within are visible.

FIG. 6 shows another embodiment in which the apparatus is enclosed within a housing 260, and a sample module 280 is loaded vertically rather than horizontally. The housing 260 has at least one vent 263 for enabling a cooling element 261 and a cooling element 262 (on the opposite side, as shown in FIG. 7) to exchange hot air within the device with cooler ambient air. Views A-D show the progression of loading a sample module 280 through a sample module port 264 into the apparatus and closing a lid 265.

FIG. 7 is a perspective view of the embodiment in FIG. 6, where the housing 260 is transparent so that the internal elements are visible. Except where otherwise stated, the major internal elements of FIGS. 7-10 operate in a fashion similar to the elements of the embodiment shown in FIGS. 1-4. For example, the first pivot arm 210, second pivot arm 220, first through fourth thermal masses 211, 212, 223, 224, first actuator 219, second actuator 229, controller 230, and cooling elements 261, 262 of FIG. 7 operate similarly to the first pivot arm 110, second pivot arm 120, first through fourth thermal masses 111, 112, 123, 124, first actuator 119, second actuator 129, controller 130, and cooling elements 161, 162 of FIGS. 1-4. A relay unit 231 contains one or more relays for switching and/or modulating current to heating elements, as dictated by the controller 230.

Figure 8:
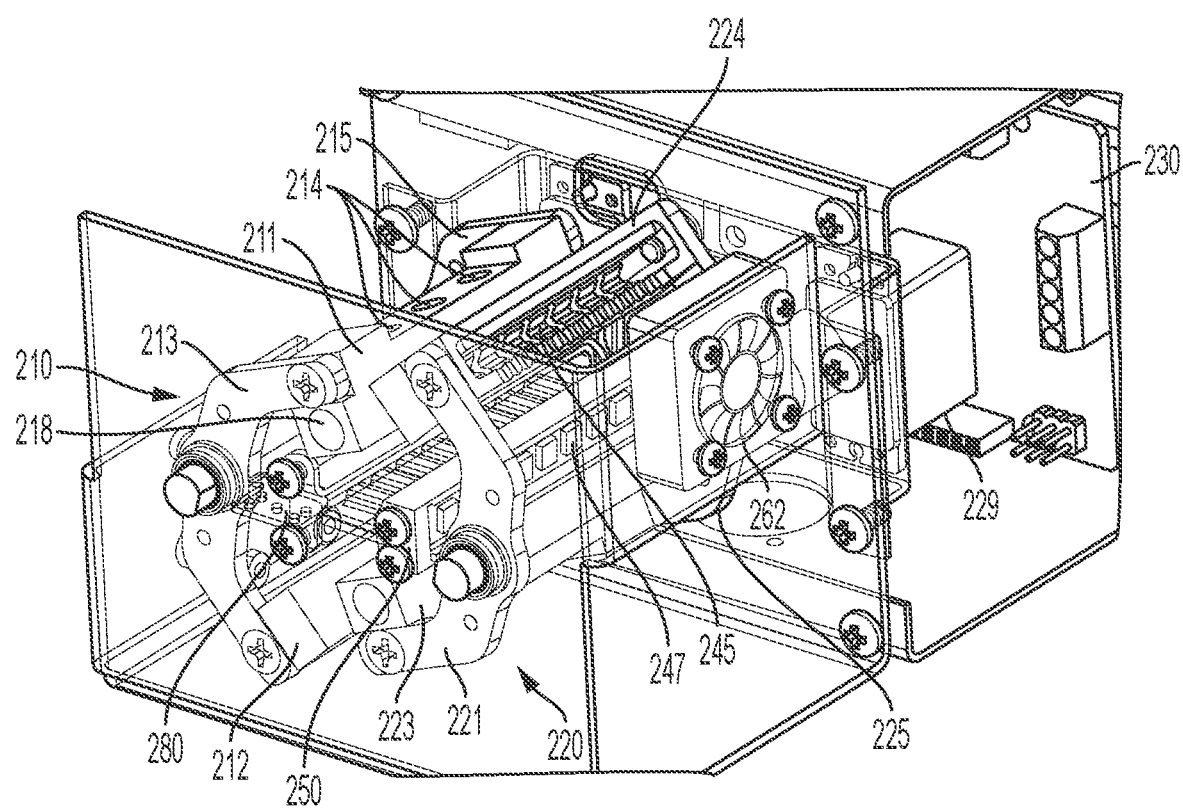
FIG. 8 is a perspective view of the embodiment of FIG. 6 with portions of the housing either removed or made transparent so elements within are visible, and where all thermal masses are unclamped from the sample module.

FIG. 8 is a perspective view of the embodiment of FIG. 6 with portions of the housing either removed or made transparent so elements within are visible, and where all thermal masses are unclamped from the sample module. In this embodiment, first thermal mass 211 and second thermal mass 212 are each coupled to first pivot arm 210, while third thermal mass 223 and fourth thermal mass 224 each coupled to second pivot arm 220. In the illustrated embodiment, first pivot arm 210 comprises a first bracket arm 213 and a second bracket arm 215. Similarly, second pivot arm 220 comprises a first bracket arm 221 and a second bracket arm 225. In this embodiment, the illumination module elements 245 A-H are contained within one of the cooling thermal masses, such as the third thermal mass 223. Small ports through the sample-module-facing side of the thermal mass 223 allow light from the illumination module elements 245 to pass through and excite fluorescent material within the sample module 280 when the cooling thermal masses are clamped around the sample module 280. A detection module 247 is embedded within one of the retaining members 250.

The detection module 247 contains one or more detection module elements 247A-H, which measure the emitted fluorescence from within the sample chambers of the sample module 280. The heating thermal masses such as the first thermal mass 211 and the third thermal mass 223 have ports 218 for heating elements, as well as one or more ports for 214 for temperature measurement probes. The temperature measurement probes can comprise but are not limited to thermocouples, resistance temperature detectors (RTDs), and thermistors. The heating elements can be controlled by the controller 230 and switched on/off using one or more relays in a relay unit 231 (shown in FIG. 9). Control of the heating elements can be based on a feedback loop with measurements from temperature measurement probes.

Figure 9:
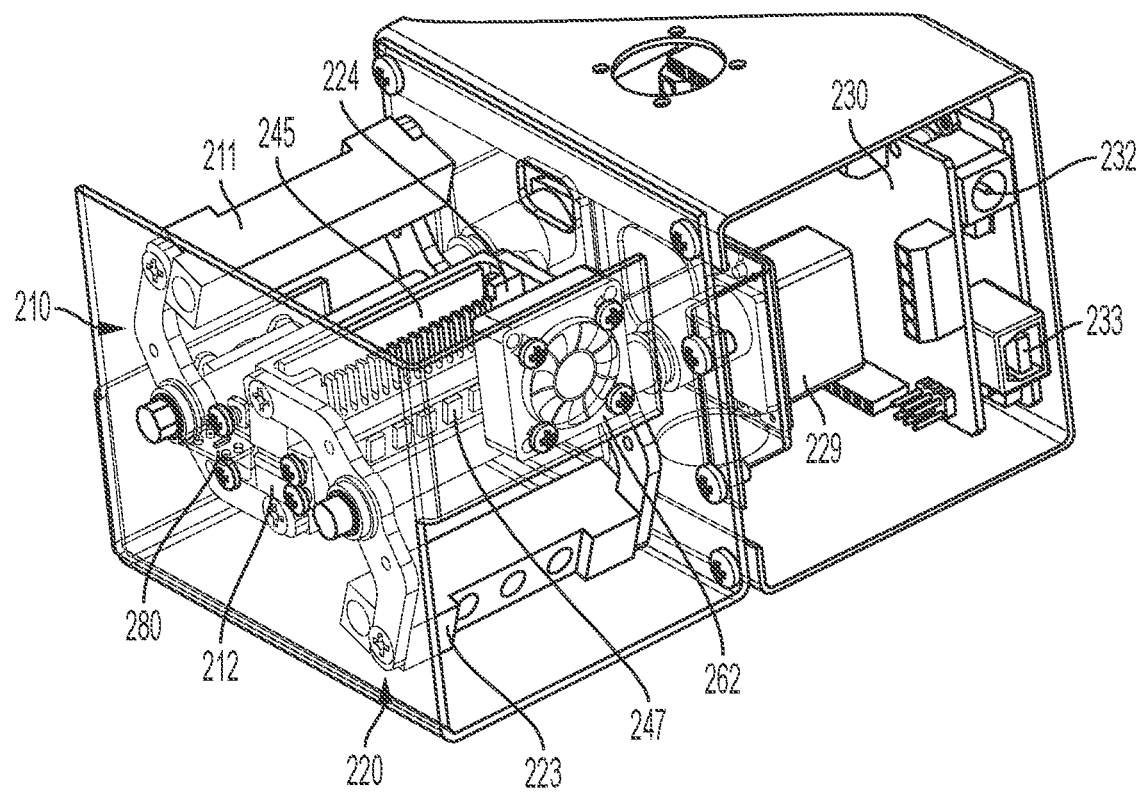
FIG. 9 is a perspective view of the embodiment of FIG. 8 where the second and third thermal masses are clamped around the sample module.

FIG. 9 is a perspective view of the embodiment of FIG. 8 where the second and fourth thermal masses are clamped around the sample module. The controller 230 receives power through a power input 232. The controller can optionally comprise a computer connector 233 for sending and/or receiving data and/or commands to or from a computer. However, other common means of connectivity can be included, such as Bluetooth and/or WiFi. Regarding cooling of the sample module 280, the cooling second and fourth thermal masses 212, 224 can optionally comprise cooling fins or other features that increase surface area for enhanced cooling.

Figure 10:
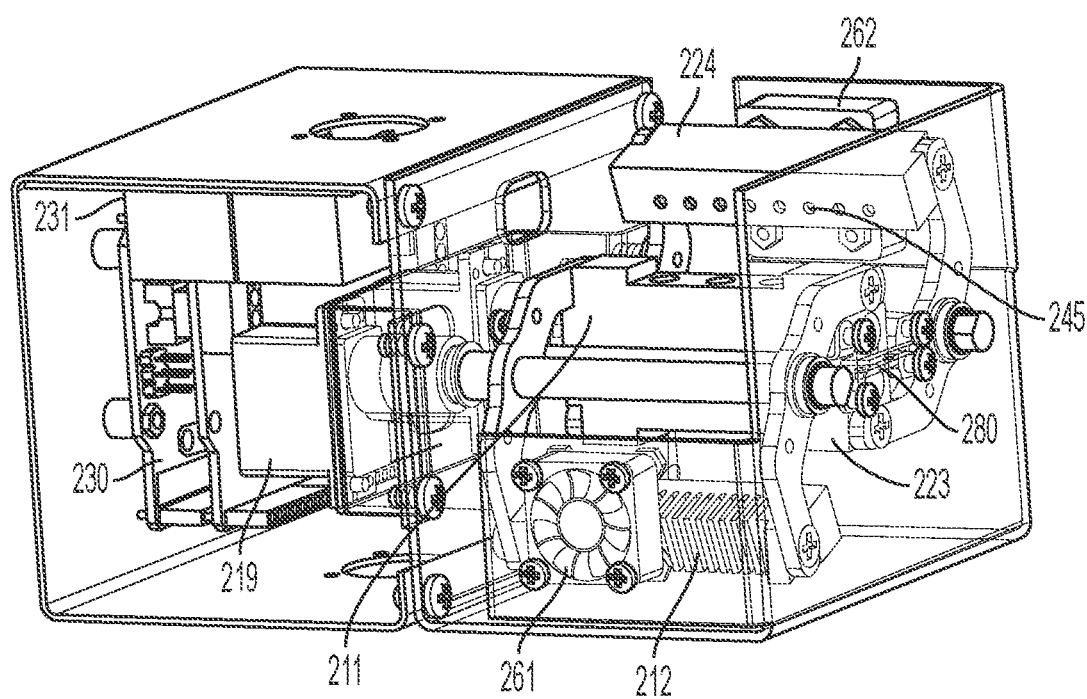
FIG. 10 is a perspective view of the embodiment of FIG. 8 where the first and fourth thermal masses are clamped around the sample module.

FIG. 10 is a perspective view of the embodiment of FIG. 8 where the first and third thermal masses are clamped around the sample module. Ports in the fourth thermal mass 224 allow light from the illumination module 245 to pass through and excite fluorescent material within the sample module 280 when the fourth thermal mass 224 is placed in optical communication with the sample module 280.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. REFERENCES

The following references, to the extent that they provide exemplary procedural or other details supplementary to those set forth herein, are specifically incorporated herein by reference.
U.S. Pat. No. 6,403,037
U.S. Pat. No. 7,466,908
U.S. Pat. No. 9,057,568
US Pat. Pub. 2008/0057544
US Pat. Pub. 2016/0289736
PCT Pat. Pub. WO2004029195
PCT Pat. Pub. WO2012161566
PCT Pat. Pub. WO2013158740
Farrar, Jared S., and Carl T. Wittwer. "Extreme PCR: efficient and specific DNA amplification in 15-60 seconds." Clinical chemistry 61.1 (2015): 145-153.

Wittwer, Carl T., G. Chris Fillmore, and David J. Garling. "Minimizing the time required for DNA amplification by efficient heat transfer to small samples." Analytical biochemistry 186.2 (1990): 328-331.

Zhang, Chunsun, and Da Xing. "Miniaturized PCR chips for nucleic acid amplification and analysis: latest advances and future trends." Nucleic acids research 35.13 (2007): 4223-4237.

Wittwer, Carl. "Extreme PCR: DNA Amplification in 15-60 Seconds," 23rd Annual Symposium on Molecular Pathology, 16 Sep. 2014, Somerset Inn, Troy, MI Keynote Address.

Shaw, Kirsty J., et al. "Rapid PCR amplification using a microfluidic device with integrated microwave heating and air impingement cooling." Lab on a Chip 10.13 (2010): 1725-1728.

Fermér, Christian, Peter Nilsson, and Mats Larhed. "Microwave-assisted high-speed PCR." European journal of pharmaceutical sciences 18.2 (2003): 129-132.

Chen, Shuqi, and Lingjun Chen. "Sample processing." U.S. patent application Ser. No. 11/674,117, filed Feb. 12, 2007.

Fuchiwaki, Yusuke, and Hidenori Nagai. "Study of a liquid plug-flow thermal cycling technique using a temperature gradient-based actuator." Sensors 14.11 (2014): 20235-20244.

Kopp, Martin U., Andrew J. De Mello, and Andreas Manz. "Chemical amplification: continuous-flow PCR on a chip." Science 280.5366 (1998): 1046-1048.

Neuzil, Pavel, et al. "Ultra fast miniaturized real-time PCR: 40 cycles in less than six minutes." Nucleic acids research 34.11 (2006): e77-e77.

Li, Zhiyong, et al. "Gold nanorod-facilitated localized heating of droplets in microfluidic chips." Optics express 21.1 (2013): 1281-1286.

Huhmer, A. F. R., and J. P. Landers. "Noncontact infrared-mediated thermocycling for effective polymerase chain reaction amplification of DNA in nanoliter volumes." Analytical chemistry 72.21 (2000): 5507-5512.

Wittwer, Carl T., Gudrun B. Reed, and Kirk M. Rine. "Rapid cycle DNA amplification." The polymerase chain reaction. Birkhäuser Boston, 1994. 174-181.

Son, Jun Ho, et al. "Ultrafast photonic PCR." Light: Science & Applications 4.7 (2015): e280.

Tanriverdi, Sultan, Lingjun Chen, and Shuqi Chen. "A rapid and automated sample-to-result HIV load test for near-patient application." Journal of Infectious Diseases 201. Supplement 1 (2010): S52-S58.

What is claimed:

1. An apparatus for thermal cycling, the apparatus comprising:
   a first thermal mass;
   a second thermal mass;
   a retaining member;
   a sample module;
   at least one actuator;
   and a
   controller, wherein:
      the controller is configured to control the at least one actuator;
      the actuator is configured to move the first thermal mass and the second thermal mass from a first position to a second position;
      the first thermal mass and the second thermal mass are in contact with the sample module in the first position;
      the first thermal mass and the second thermal mass are not in contact with the sample module in the second position;
      the retaining member is configured to retain the sample module in a fixed position as the as the actuator moves the first thermal mass and the second thermal mass from the first position to the second position; and
      the sample module comprises:
         a core layer;
         a first film bonded to the core layer;
         a second film bonded to the core layer;
         an inlet;
         a channel in fluid communication with the inlet;
         a plurality of sample chambers in fluid communication with the channel; and
         a plurality of air spring chambers containing air.

2. The apparatus of claim 1 wherein the plurality of air spring chambers is configured such that the air contained in the plurality of air spring chambers is compressed by a flow of fluid from the channel into the plurality of sample chambers.

3. The apparatus of claim 2 wherein the core layer has a thickness of about 0.5 millimeters (mm) to 1.5 mm.

4. The apparatus of claim 3 wherein the first film has a thickness of 10 micrometers (μm) to 30 μm.

5. The apparatus of claim 4 wherein the second film has a thickness of 10 μm to 30 μm.

6. The apparatus of claim 1 wherein the first film is sufficiently flexible to conform to a first surface of the first thermal mass and the second film is sufficiently flexible to conform to a second surface of the second thermal mass.

7. The apparatus of claim 1 wherein:
   the retaining member comprises a detection module;
   each sample chamber of the plurality of sample chambers has a length and a width, wherein the length is greater than the width; and
   the detection module is configured to detect a response signal through an edge of the core layer and parallel to the length of each sample chamber of the plurality of sample chambers.

8. The apparatus of claim 1 wherein the retaining member comprises an illumination module and a detection module.

9. The apparatus of claim 7 wherein:
   each sample chamber of the plurality of sample chambers has a length and a width, wherein the length is greater than the width;
   the illumination module is configured to emit an excitation signal parallel to the length of each sample chamber of the plurality of sample chambers; and
   the detection module is configured to detect a response signal parallel to the length of each sample chamber of the plurality of sample chambers.

10. The apparatus of claim 8 wherein the illumination module comprises a plurality of illumination elements, and wherein each illumination element is configured to illuminate a sample chamber of the plurality of sample chambers.

11. The apparatus of claim 10 wherein the plurality of illumination elements comprises light emitting diodes (LEDs).

12. The apparatus of claim 1 wherein:
   the plurality of sample chambers comprises a first sample chamber;
   the plurality of air spring chambers comprises a first air spring chamber; and the first sample chamber and the first air spring chamber form a "U" shape comprising a first arm and a second arm.

13. The apparatus of claim 12 wherein the air spring chamber is configured such that the air contained in the air spring chamber is compressed by a flow of a sample from the first arm to the second arm.

* * * * *